United States Patent [19]

Bartholomew

[11] 4,201,205

[45] May 6, 1980

[54] OXYGEN MASK

[75] Inventor: Victor L. Bartholomew, Hemet, Calif.

[73] Assignee: Hudson Oxygen Therapy Sales Company, Temecula, Calif.

[21] Appl. No.: 871,151

[22] Filed: Jan. 20, 1978

[51] Int. Cl.² .............................................. A61M 15/00
[52] U.S. Cl. ............................ 128/205.25; 128/207.11
[58] Field of Search .............. 128/205, 206, 207, 208, 128/212, 185, 195, 198, 146, 146.2, 146.6, 146.7, 140 N, 203; 2/206, 9; D29/8, 9; D24/2

[56] References Cited

U.S. PATENT DOCUMENTS

| D. 250,131 | 10/1978 | Lewis et al. | 128/146.7 X |
|---|---|---|---|
| 2,208,633 | 7/1940 | Heidbrink | 128/203 |
| 2,675,803 | 4/1954 | Kaslow | 128/205 |
| 3,013,556 | 12/1961 | Galleher, Jr. | 128/146.7 |
| 3,172,407 | 3/1965 | Pechmann | 128/206 |
| 4,106,505 | 8/1978 | Salter et al. | 128/206 |

Primary Examiner—Henry J. Recla
Attorney, Agent, or Firm—Seiler and Quirk

[57] ABSTRACT

In an oxygen mask for being secured over the nose and mouth of a user or patient, an improved means for securing the mask comprises a non-elastic flexible tubing adapted for extending over both ears of the user, ends, and two lengths of elastic flexible tubing, each length having one end secured to the non-elastic tubing, and the other end secured to or adjacent the mask.

12 Claims, 4 Drawing Figures

OXYGEN MASK

BACKGROUND OF THE INVENTION

Oxygen masks have traditionally been secured to a patient or user with a length of elastic strap extending through openings on opposite sides of a mask, for example, as disclosed in U.S. Pat. Nos. 2,843,121 and 2,859,748. The mask is secured to the patient by placing the strap around the patient's head, normally under the ears. Although such elastic strap can be adjusted to maintain the mask fit against the patient's face, normally over the nose bridge, across and around the cheeks, and under the lips or chin, there are associated disadvantages. For example, the placing of the strap around the patient's head is often undesirable because it requires movement of the patient's head in so securing the mask, contrary to preferred practice, especially where there is possible back, head or neck injury. Moreover, with the patient lying with his or her head resting on a pillow, the strap around the head, between the pillow and the patient's lower head or neck, causes discomfort, especially if the mask is worn for a substantial period of time.

An alternative means for securing an oxygen or gas delivery mask on a user or patient comprises incorporating a pair of oxygen or gas delivery tubes into the mask, which tubes are then placed over and around the patient's ears, and using some tying or restricting means for holding the tubes together beneath the chin. This type of means for securing a mask is shown and disclosed in U.S. Pat. No. 2,675,803, where two gas delivery tubes themselves are placed over the patient's ears. Although such means obviates the elastic strap problem around the patient's head, as previously described, it presents other disadvantages. For example, where an elastic rubber or synthetic elastomer tubing is used around the patient's ears, skin irritation and chafing results where the elastic contacts the patient's skin, because of the periodic stretching or flexing of the tubing. Such stretching and return of the elastic causes the skin to be alternately stretched and pinched along with the tubing, so that when such a mask is worn for any extended length of time, user or patient discomfort may be significant.

Where the tubing is of a non-elastic quality, such as polyvinyl chloride, although flexible, the tubing will not yield sufficiently along its length to achieve sufficient security or fit for the mask. For example, where the mask is properly secured on a patient's face initially, as the patient or user moves his or her head about on the pillow, or during any other facial movement, the non-elastic tubing will become loosened, but will not return back to its original tension to secure the mask against the user's face. Thus, after a period of time, the mask becomes so loosened, as to not be effective in providing necessary oxygen concentration deliveries to the patient or user, without repeated and aggravating adjustment. It is to the elimination of the aforementioned disadvantages that the present invention is directed.

SUMMARY OF THE INVENTION

The mask of the present invention incorporates an improved means for being secured to a user. This improvement comprises, in combination, non-elastic flexible tubing, which extends over and around the user's ears and is brought under the chin, where it is tightened by using an adjustable ring or clip, and a length of elastic tubing attached on or adjacent opposite sides of the mask, as well as to the non-elastic tubing. The elastic tubing provides continuous fit of the mask because of the spring-like qualities of the elastomer, without requiring repreated manual adjustment, but does not extend over the patient's ears, thereby preventing irritation problems. These as well as other advantages of the mask and the more specific features thereof will be readily understood from the following detailed description.

DETAILED DESCRIPTION OF THE INVENTION

Figure 1:
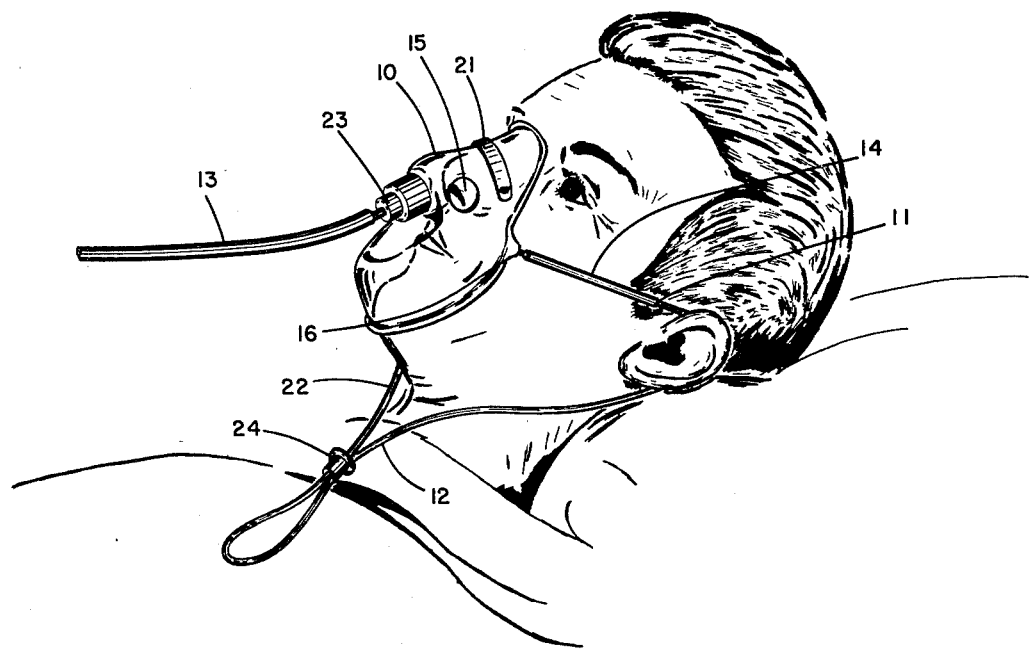
FIG. 1 is a perspective view showing one embodiment of the improved mask of the invention, positioned on a user.
Figure 2:
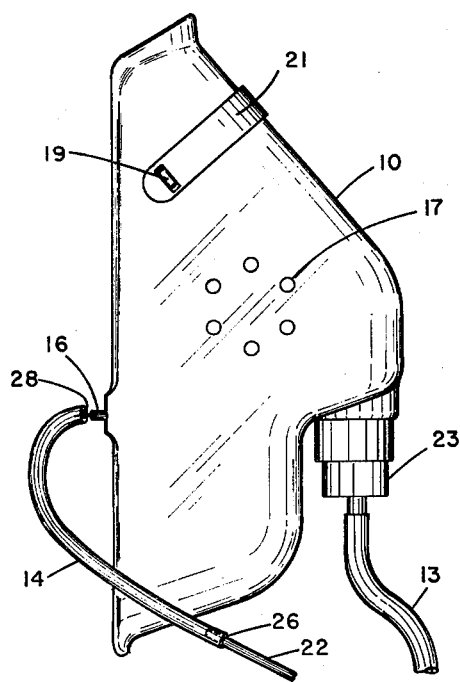
FIG. 2 is a side view of the mask of FIG. 1; showing means for attaching elastic tubing to the mask.
Figure 3:
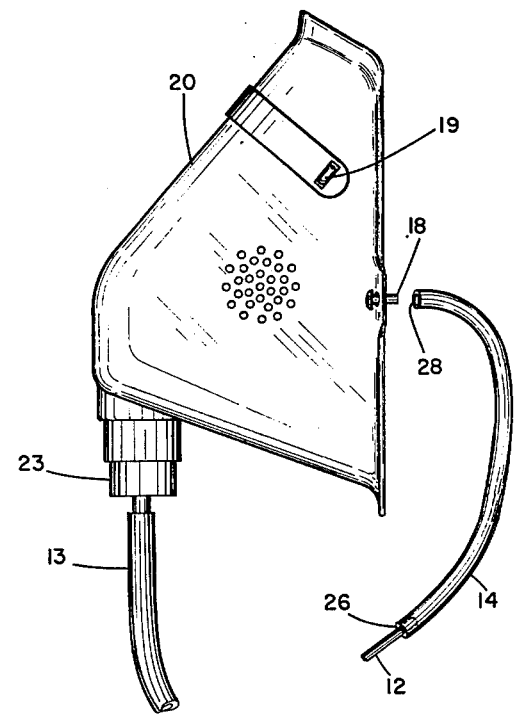
FIG. 3 is a side view of a different mask, showing an alternative means for securing elastic tubing to the mask.

The mask 10 in FIG. 1 is used, as shown, overlying the patient's face, over the nose bridge, cheeks, and under the chin. Such a mask is referred to as an "elongated" mask, normally used for the edentulous patient. The same elongated mask is shown in FIG. 2, while the mask in FIG. 3 is designed to extend under the patient's or user's mouth, but above the chin. Any type of similar masks may be used with the improved securing means of the present invention, including a mask or face shield having an open bottom such as disclosed in co-pending application Ser. No. 737,851, filed Nov. 1, 1976. Such masks normally are made of a relatively soft, resilient and flexible material such as PVC (polyvinyl chloride) or other suitable and equivalent material. The most commonly used composition is a medical grade or FDA approved PVC which has been compounded with plasticizers, normally phthalates, such as DOP (dioctyl phthalate) or equivalent compounds. The peripheral mask edges often incorporate an out-turned flange to achieve a more effective and comfortable gas seal with the patient's face along the area of the contact with the mask. Such masks also include different shaped holes or orifices 15, 17, normally adjacent the patient's or user's nose, and a breathing bag (not shown), depending on desired oxygen concentration delivered to a patient.

In the mask examples shown, a soft metal strip 21 is secured to the exterior mask surface, which strip can be easily bent to assist the mask in forming to the general contour of the patient's face, over the nose bridge. For this use, an aluminum strip may be preferred, so that it can be easily formed to the desired fit once the mask is placed on the patient. The strip is secured to the mask by one or more tabs or protuberances 19, formed on the exterior mask surface, and which extend through openings formed in the strip. Also in the masks shown, are gas delivery tubes 13 which are fitted onto an adapter plug 23, which plug is fitted into an enlarged gas delivery orifice in the mask. Such masks, as well as other features thereof, are well known to those skilled in the art and need not be described further herein.

FIGS. 1 and 2 illustrate an embodiment incorporating the improved means for securing the masks on the user or patient. For this purpose, a length of elastic flexible tubing 14 extends across the patient's cheeks, with one end of the tubing being secured with tab member or appendage 16, which is integral with mask 10. The elastic tubing length 14 terminates at end 11, at which is secured an end of non-elastic flexible tubing 12. A substantially identical tab is located on the opposite side of the mask as is a length of elastic tubing 14 as is shown in FIG. 2.

A tab 16, located adjacent each side of the mask adjacent the peripheral mask edge, is integrally formed with the mask in the mold, and accordingly is of the same material, preferably PVC, as previously explained. The shape of the tab is not critical, except that it should be easily inserted into the end of elastic tubing 14, and secured therein. The tab 16 and end 28 of elastic tubing 14 may be joined by any suitable means, the use of a common solvent for adhering the two materials being an easy method joining them. The length of elastic tubing 14 should be such that it extends sufficiently to provide an elastic piece that can be stretched when non-elastic tubing 12 and 22 are tightened or taut, whereby the mask is pulled comfortably, but securely, against the patient's face. Again, because of the elastic properties of flexible tubing length 14, this securing of the mask will be maintained even though the patient or user moves his or her head about, yawns, etc., thereby causing some stretching or recovery of the elastic tubing.

Suitable elastic tubing compositions include natural rubber or synthetic elastomers having rubber-like characteristics. Such synthetics include styrene-butadiene copolymers (SBR), polybutadiene, neoprene, butyl, polyisoprene, nitrile (acrylonitrile-butadiene copolymers), ethylene-propylene, polyester (Hytrel), polyolefin (TPR), and even silicone or nitrile-silicone rubbers. The above list is not intended to be exhaustive of the synthetic polymeric elastomers which may be used to form the flexible elastic tubing used in the invention, but is given by way of illustration only. Preferred is natural rubber, as is a thermoplastic elastomer comprising block copolymer structure of rigid polystrene end blocks with elastomeric polybutadiene or polyisoprene center blocks, and marketed as Kraton. However, such preferred materials are also those which are readily adhered to the integral PVC tab, or other means secured to the mask for attaching the elastic tubing. Thus, those materials which are readily adhered by a common solvent, or the like are most suitable and which have good elastic properties and meet medical grade or FDA requirements.

The non-elastic tubing, which is attached to the end of the elastic tubing, and which non-elastic material extends over and around the user's ears, preferably comprises a medical grade or FDA approved polyvinyl chloride, normally substantially like the material used in producing the mask, as previously described. Such tubing may be catheter stock with material having outer diameters of between about two and about four mm, being especially useful and readily commercially available. Similar tubing is often used in delivering oxygen enriched gases to patients, and is sometimes referred to as narine tubing. The significant distinction between this non-elastic tubing and the elastic tubing lengths, previously described, for extending from the mask but stopping short of the patient's ear, is that the non-elastic tubing, although quite flexible and resilient, is not capable of substantial expansion along its length, and thereafter rapidly returning to any original unexpanded condition. As is illustrated in FIGS. 1-3, the non-elastic tubing 12, 22, may actually be a single length of tubing used in a manner shown in FIG. 1, which is tightened by use of a sleeve member or ring 24, below the patient's chin. However, two individual non-elastic tube lengths may be used, and tied or otherwise joined together, as desired in this embodiment.

FIG. 3 illustrates an alternative embodiment of securing the elastic tubing length to mask 20, by using a rivet or pin member 18, having an expanded head on one side and extending through an opening in the mask, adjacent to the peripheral edge, and on which rivet is secured end 28 of elastic tubing length 14. The rivet may be prepared of any material, including PVC, polyethylene, or the like, selected so as to be readily adhered to the elastic tubing, such as by using a common solvent. Common solvents such as methlyene dichloride, MEK, dichlorobenzene, or any other materials, known to those skilled in the art, may be used to achieve surface bonding of most of the materials disclosed. The securing of the two ends of the elastic tubing with the mask, and with the non-elastic tubing, is most easily accomplished in an assembly line operation, with the solvent also selected for quick drying and yet firm surface bonding.

The embodiments illustrated in FIGS. 1-3 are those in which the tubing used for securing the mask to the user or patient, is not for directing oxygen into the mask. Instead, as previously noted, oxygen supply tubing 13 is connected to an oxygen or oxygen enriched gases source, and oxygen so supplied to the mask rather than through the non-elastic tubing lengths 12 and 22, and elastic tubing lengths 14. However, according another embodiment of the invention illustrated in FIG. 4, the tubing means for securing the mask may also be the means for delivering oxygen or gas. As shown non-elastic tubes 40 and 44, are secured to elastic tubing lengths 34 and 36, each of which lengths are secured at opposite sides of the mask 30 to a gas inlet member 35 and 38, respectively. The mask shown also includes a gas delivery means secured on the mask interior surface comprising a gas delivery pipe 32. This pipe is hollow, and is provided with a plurality of openings or orifices 33 through which oxygen containing or other gas is delivered into the mask. At each end of the pipe are gas inlets 35 and 38, and which communicate interioriolly of pipe 32, as well as with hollow elastic tubing lengths 34 and 36. Opposite ends of the elastic tubing are secured to the non-elastic tubing and gas inlet members, respectively. This may be accomplished as previously explained using a common solvent for surface bonding the materials.

The gas delivery pipe 32 may be secured to mask 30 by any suitable means, such as by adhesives, surface bonding by common solvents, and the like. Alternatively, a flexible clamp member 41, integral with the mask, or other channel means, formed on the interior mask surface, may be used. The incorporation of such a means will allow the gas delivery pipe to be positioned and held along the interior mask surface, and yet the pipe can be easily put in such a channel by simply inserting or snapping it into place during assembly. The mask will also be provided with orifices adjacent each peripheral side through which the gas inlets extend and for attaching the ends of the respective elastic tube members 34 and 36. The gas delivery pipe may be formed of a more rigid material, for example rigid PVC, polyethylene, polypropylene, or any other desired or approved material.

Figure 4:
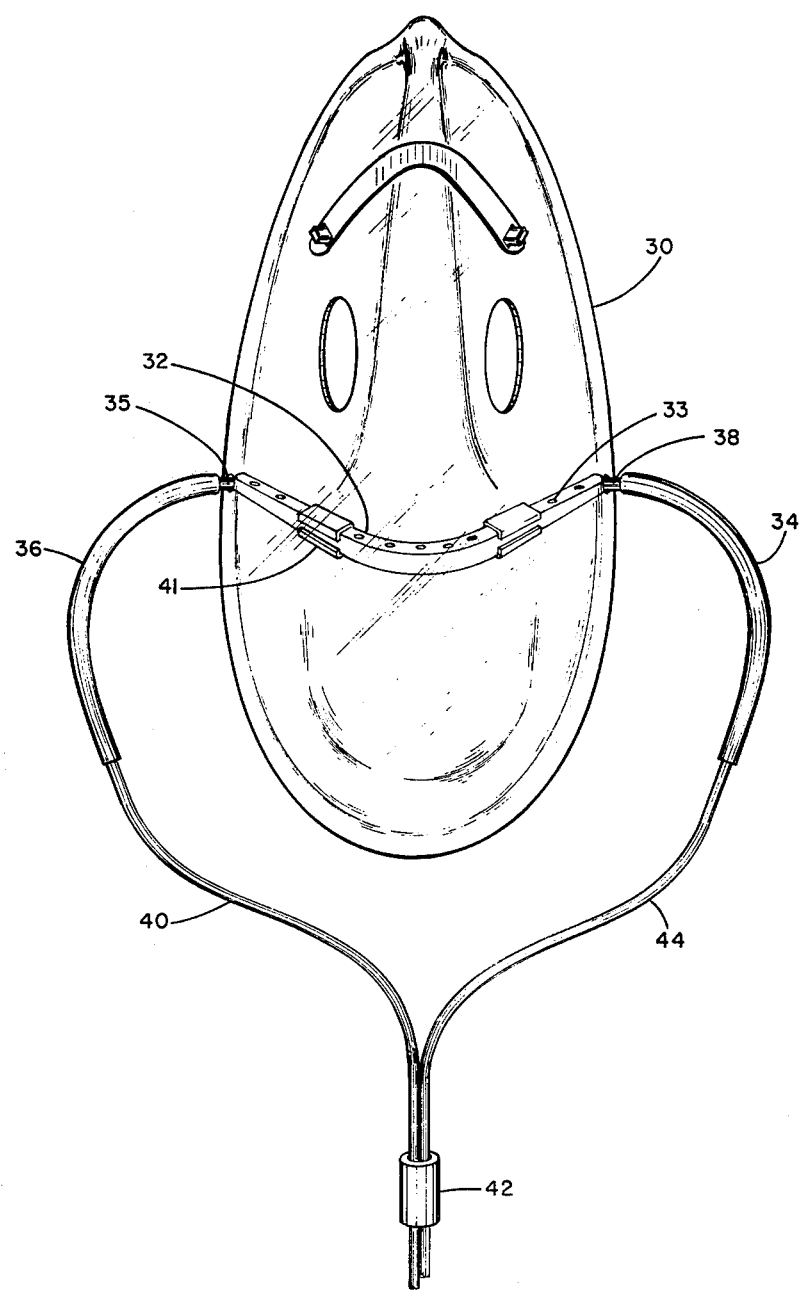
FIG. 4 is a front view showing still another embodiment in which the elastic and non-elastic tubing for securing the mask on a user also supply gas to the mask.

The mask illustrated in the FIG. 4 embodiment is secured on a patient in a manner like that described and shown with the previous embodiments. Thus, the mask is simply placed over the patient's face, and the non-elastic tubing 40 and 44 extended over and around the patient's ears and brought together under the chin, where a slideable sleeve 42 may be tightened or loosened for comfortably fitting the mask as previously described. With the ends of the non-elastic tubes being secured and connected to an oxygen or oxygen containing gas delivery source, no further oxygen tubes are needed for providing gas to the patient, nor are other straps necessary for securing the mask on the patient. These as well as other advantages of the various embodiments as well as modifications thereof within the purview of the invention will be evident to those skilled in the art.

I claim:

1. An oxygen mask having improved means for being secured over the nose and mouth of a user, the improvement comprising;
non-elastic flexible tubing means adapted for extending over and behind both ears of the user and downwardly beneath the user's chin and having two ends, and two lengths of elastic flexible tubing, each length having a first and second end, each first end being secured to a different one of said non-elastic tubing ends, and means securing each second end of said elastic flexible tubing to said mask and wherein said non-elastic tubing ends and said first elastic tubing ends are adapted to be joined between said mask and the user's ears.

2. The mask of claim 1 wherein said non-elastic tubing comprises polyvinyl chloride.

3. The mask of claim 2 wherein said elastic tubing comprises a synthetic elastomer or natural rubber.

4. The mask of claim 3 wherein said mask comprises polyvinyl chloride.

5. The mask of claim 1 wherein said means securing said second ends to said mask comprises first and second tab members integral with and each extending from an opposite side of said mask, said second ends being secured to said first and second tab members, respectively.

6. The mask of claim 5 wherein said non-elastic flexible tubing comprises a single length of tubing.

7. The mask of claim 5 wherein said mask and said non-elastic tubing comprise polyvinyl chloride.

8. The mask of claim 7 wherein said elastic tubing comprises a synthetic elastomer or natural rubber.

9. The mask of claim 1 wherein said means securing said second ends to said mask comprises first and second pin members each secured along an opposite side of said mask, said second ends being secured to first and second pin members, respectively.

10. The mask of claim 6 wherein said non-elastic flexible tubing comprises a single length of tubing.

11. The mask of claim 6 wherein said mask and said non-elastic tubing comprise polyvinyl chloride.

12. The mask of claim 1 wherein said elastic tubing comprises a synthetic elastomer or natural rubber.

* * * * *